United States Patent [19]

Takeuchi et al.

[11] Patent Number: 5,093,323
[45] Date of Patent: Mar. 3, 1992

[54] ANTIBIOTIC N-ACETYLBENANOMICIN B, AND THE PRODUCTION AND USES THEREOF

[75] Inventors: Tomio Takeuchi, Tokyo; Shinichi Kondo, Yokohama; Shuichi Gomi, Tokyo; Hiroo Hoshino, Maebashi, all of Japan

[73] Assignee: Zaidan Hojin Biseibutsu Kagaku Kenkyu Kai, Tokyo, Japan

[21] Appl. No.: 459,352

[22] Filed: Dec. 29, 1989

[30] Foreign Application Priority Data

Jan. 13, 1989 [JP] Japan ................................. 1-4701

[51] Int. Cl.$^5$ .................. A61K 31/71; A61K 31/70; C07H 15/252
[52] U.S. Cl. ............................. 514/34; 514/33; 514/53; 536/4.1; 536/6.4; 536/17.2; 435/238
[58] Field of Search .................... 514/33, 53, 34; 536/4.1, 6.4, 17.2, 16.8, 18.1; 435/238

[56] References Cited

U.S. PATENT DOCUMENTS 4,973,673 11/1990 Sanada et al. ............... 536/17.2
5,055,453 10/1991 Takeuchi et al. .............. 514/27

FOREIGN PATENT DOCUMENTS 0277621 8/1988 European Pat. Off. .
0315147 5/1989 European Pat. Off. .
0378126 7/1990 European Pat. Off. .

OTHER PUBLICATIONS

T. Oki et al., The Journal of Antibiotics, "Pradimicin, a Novel Class of Potent Antifungal Antibiotics", vol. 41(11) 1988 Nov., pp. 1701-1704.

T. Takeuchi et al., Chemical Abstracts, "New Antifungal Antibiotics, Benanoiciness A and B, from an Actinomycete", vol. 100, No. 15, Oct. 10, 1988, p. 357, col. 1, Abstract-No. 125 508x & J. Antibiotics 41(6):807-811 (1988-Jun.).

The Merck Manual, 15th Edition; pp. 158-168 (1987).
Gomi et al; J. Antibiotics 41(8):1019-1028 (1988-Aug.).

Primary Examiner—Johnnie R. Brown
Assistant Examiner—Nancy S. Carson
Attorney, Agent, or Firm—Larson and Taylor

[57] ABSTRACT

As a new compound is now provided N-acetylbenanomicin B which is useful as an antifungal agent and also as antiviral agent for inhibiting infection of human T-cell with HIV, namely a virus causative of acquired human immunodeficiency syndrome. N-acetylbenanomicin B may be prepared by acetylation of 4″-amino group of benanomicin B which is fermentatively produced by a new microorganism, MH193-16F4 strain of actinomycetes.

10 Claims, No Drawings

ANTIBIOTIC N-ACETYLBENANOMICIN B, AND THE PRODUCTION AND USES THEREOF

SUMMARY OF THE INVENTION

This invention relates to a new antibiotic, N-acetylbenanomicin B, which has an antifungal activity and an antiviral activity and which is useful as a therapeutic antifungal agent and also an antiviral agent and may be present also in the form of its salts or its esters. This invention also relates to pharmaceutical compositions comprising N-acetylbenanomicin B as active ingredient. This invention further relates to a process for the production of N-acetylbenanomicin B.

BACKGROUND OF THE INVENTION

Many antibiotics are already known but new antibiotic substances are still demanded to be provided in the pharmaceutical field and also in the agricultural field. Compounds which are similar in their structural feature of the molecule to the new antifungal and antiviral antibiotic, N-acetylbenanomicin B now newly provided by the present inventors are benanomicin A and benanomicin B as well as dexylosylbenanomicin B which have hithertobefore been obtained as new compounds by the present inventors (see Japanese patent applications Nos. 277,692/87 and 327,163/87 as laid-open under Japanese patent application first publications "Kokai" No. 121,293/83 published on 12 May, 1989 and No. 254,694/89 published on 11 October 1989, respectively, as well as their corresponding European patent application publication No. 0 315 147 A2 published on 10 May 1989 and corresponding U.S. patent application Ser. No. 264,888 filed on 31 October 1988 now U.S. Pat. No. 5,055,453). Furthermore, KS-619-1 substance [Matsuda et al: the "Journal of Antibiotics" 40, 1104–1114(1987)], G-2N substance and G-2A substance [Gerber et al: "Canada. J. Chem," 62, 2818–2821 (1984)] as well as pradimicins A, B and C [Oki et al: "Journal of Antibiotics" 41, 1701–1704 (1988); Tsunakawa et al: "J. Org. Chem." 54, 2532–2536 (1989); and European patent application publication No. 0 277 621] are already known. Among them, benanomicin B seems to be identical to pradimicin C by their structural studies.

Hithertobefore, a variety of antibiotics which are produced by microorganisms are already known. Among the known antibiotics, however, such antibiotics which can exhibit a useful antifungal activity but a low toxicity to mammals are only few. Accordingly, there is always a demand for discovery and exploitation of a new antifungal antibiotic which is useful in the therapeutic treatment of various fungal infections in an animal, including human.

On the other hand, acquired human immunodeficiency syndrome (sometime called merely as "AIDS") has been found to be a disease which is caused due to human T-cells being infected by a causative virus in human blood. The virus which is causative of the acquired human immunodeficiency syndrome is usually termed as acquired human immunodeficiency syndrome virus which is often abbreviated as HIV. It has been reported that certain known compounds are useful as an agent for inactivating HIV or an antiviral agent against HIV. However, any of these compounds is not necessarily satisfactory as a useful remedial agent for AIDS, and there is a strong outstanding demand to develop and provide such a new drug which shows a low toxicity but can show a high activity to inactivate HIV and which are expectable as a useful medicinal agent for therapeutically or preventively treating AIDS.

According to some inventions which are earlier made by the present inventors, there are provided two antibiotics, benanomicin A and benanomicin B, which each have an antifungal activity and an HIV-inactivating activity, as well as a process for the production of benanomicins A and B by cultivation of an actinomycete strain MH193-16F4 (deposited under FERM BP-2051)(see the above-mentioned European patent application publication No. 0 315 147 A2 and its corresponding U.S. patent application Ser. No. 264,888 now U.S. Pat. No. 5,055,453). Furthermore, there is provided a pharmaceutical compositions for inactivating HIV virus, which comprises benanomicin A or benanomicin B as active ingredient (see Japanese patent application No. 206346/88, filed on 22 August 1988 and its corresponding European patent application No. 89.402315.9 filed on 21 August 1989 and corresponding U.S. patent application Ser. No. 394,539 filed on 16 August 1989). The chemical structure of benanomicin B is shown by the following formula (II)

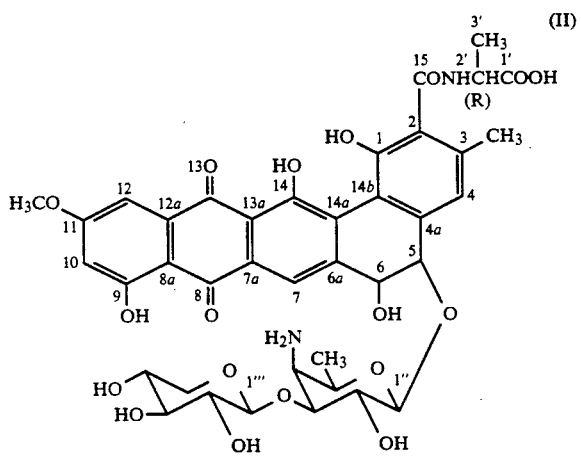

DETAILED DESCRIPTION OF THE INVENTION

We, the present inventors, have now found that when the amino group at 4"-position of benanomicin B is chemically acetylated, N-acetylbenanomicin B represented by the formula (I)

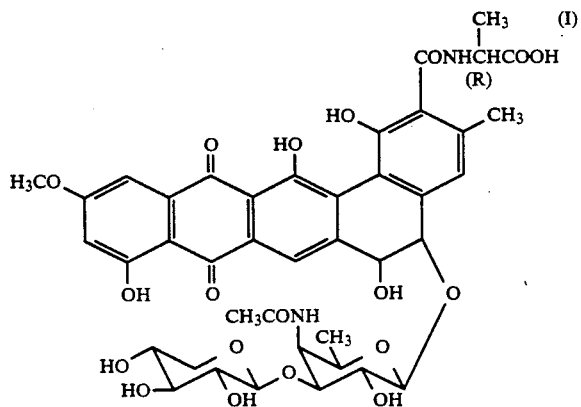

can be produced, which exhibits a reduced toxicity as compared to that of the parent benanomicin B and also shows an increased antifungal activity against some strains of fungi as compared to the parent benanomicin B. We have also found that N-acetylbenanomicin B shows an improved antiviral activity in addition to the antifungal activity. We have studied the physicochemical and biological properties of N-acetylbenanomicin B to confirm that N-acetylbenanomicin B is a new substance clearly distinguishable from any of the known antibiotics. Thus, we have acomplished this invention.

An object of this invention is to provide N-acetylbenanomicin B and salts and esters thereof as new antibiotic which has an antifungal activity and an antiviral activity but shows a low toxicity. Another object of this invention is to pvovide a process for the production of N-acetylbenanomicin B. Further objects of this invention will be clear from the following descriptions.

According to a first aspect of this invention, therefore, there is provided a new antifungal and antiviral antibiotic, N-acetylbenanomicin B having the formula (I) shown above, or a salt or an ester of N-acetylbenanomicin B.

N-acetylbenanomicin B according to this invention has the under-mentioned characteristics:

1. Physicochemical properties of N-acetylbenanomicin B are listed below.

(1) Color and appearance: Reddish brown powder (2) Elemental analysis: Calculated (for $C_{41}H_{44}N_2O_{19}.2H_2O$): C 54.42%, H 5.35%, N 3.10%
Found: C 54.05%, H 5.43%, N 2.86%

(3) Mass spectrum (SIMS): m/z 868 (M+)

(4) Melting point: >200° C.

(5) Ultraviolet and visible-ray absorption spectrum $\lambda max$, nm ($E^{1\%}_{1\ cm}$):

[In methanol]: 205(564), 229(517), 270(sh, 330), 290(403), 300(sh, 355), 400(sh, 100), 468(156)

[In 0.1 N HCl-methanol]: 208(488), 233(528), 270(sh, 325), 294(446), 400(sh, 115), 458(175)

[In 0.1 N NaOH-methanol]: 215(1233), 248(540), 319(245), 496(227)

(6) Infrared absorption spectrum (KBr, $CM^{-1}$):
3360, 2970, 2910, 1720,
1620, 1600, 1540, 1490,
1440, 1370, 1330, 1290,
1250, 1230, 1205, 1160,
1070, 1040, 1000, 970,
870, 830, 800, 740

(7) $^1$H-NMR spectrum (400 MHz, in DMSO-$d_6$, at 40° C.):

δ (ppm): 0.98(3H, d), 1.35(3H, d), 1.92(3H, s), 2.33(3H, s), 3.06(1H, dd), 3.08(1H, dd), 3.15(1H, dd), 3.29(1H, ddd), 3.70(1H, dd), 3.71(1H, br q), 3.74(1H, dd), 3.81(1H, br), 3.95(3H, s), 4.21(1H, br dd), 4.42(1H, d), 4.43(1H, dq), 4.56(1H, br d), 4.61(1H, br d), 4.64(1H, br d), 6.91(1H, d), 7.24(1H, br s), 7.28(1H, d), 7.61(1H, br d), 8.07(1H, s), 8.45(1H, d), 12.80(1H, br s), 13.82(1H, br)

(8) $^{13}$C-NMR spectrum (100 MHz, in DMSO-$d_6$, at 40° C.):

δ (ppm): 187.5 s. 184.9 s, 173.9 s, 169.9 s,
166.9 s, 166.0 s, 164.7 s, 156.8 s,
151.1 s, 147.8 s, 137.9 s, 137.3 s,
134.0 s, 131.3 s, 127.5 s, 125.6 s,
118.8 d, 115.5 s, 115.5 s, 113.7 s,
110.0 s, 107.6 d, 106.9 d, 104.9 d,
104.7 d, 81.8 d, 80.2 d, 75.8 d, 73.3 d,
71.7 d, 70.5 d, 69.9 d, 69.3 d, 65.4 t,
56.4 q, 52.0 d, 47.6 d, 22.5 q, 19.1 q,
16.9 q, 16.4 q (9) Solubility: Only sparingly soluble in chloroform, ethyl acetate and acetone, and soluble in alkaline water, methanol, dimethyl sulfoxide and dimethyl-formamide.

(10) Distinction between the basic, acidic and neutral natures of substance: Weakly acidic substance.

2. Antifungal activity of N-acetylbenanomicin B is now described.

The minimum inhibitory concentrations of N-acetylbenanomicin B against a variety of fungi were determined by a standard serial dilution method on a nutrient agar medium containing 1% glucose (pH 7.0) and are shown in Table 1 below. For comparison purpose, the minimum inhibitory concentrations of benanomicin B against the fungi were determined in the same manner as above and are shown in Table 1, too.

TABLE 1

| Micro-organism tested (fungi) | Minimim inhibitory concentrations (μg/ml) | |
|---|---|---|
| | N-acetyl-benanomicin B | Benanomicin B (Comparative) |
| Candida tropicalis F-1 | 50 | >100 |
| Candida pseudotropicalis F-2 | 12.5 | 6.25 |
| Candida albicans 3147 | 50 | 25 |
| Candida Yu-1200 | 50 | 12.5 |
| Candida krusei F-5 | >100 | 6.25 |
| Saccharomyces cerevisiae F-7 | 12.5 | 12.5 |
| Cryptococcus neoformans F-10 | 50 | 1.56 |
| Cochliobolus miyabeanus | 50 | >100 |
| Pyricularia oryzae | >50 | 50 |
| Pellicularia sasakii | 25 | 50 |
| Xanthomonas citri | 50 | >100 |
| Xanthomonas oryzae | >25 | >100 |
| Aspergillus niger F-16 | >50 | >100 |
| Trichophyton asteroides 429 | 50 | 25 |
| Trichophyton mentagrophytes (883) | 50 | 25 |

3. Activity of N-acetylbenanomicin B to inhibit infection with HIV is now tested.

Thus, the following assay tests were conducted in order to demonstrate that N-acetylbenanomicin B has an inhibitory activity to infection of human T-cells with HIV, namely the acquired human immunodeficiency syndrome virus. The procedure for these assay tests is as follows:

Effects of N-acetylbenanomicin B inhibitory against infection of human T-cells with HIV were examined in a similar manner to the assay methods described in the "Proc. Natl. Acad, Sci. USA," 80, 6061-6065 (1983); "J. Antibiot.", 40, 1077-1078, (1987); and "J. Antibiot.", 42, 344-346, (1989).

About $1 \times 10^5$ cells/ml of MT-4 cells (human T-cell line) in phosphate buffered saline were seeded into Costar 48-well plates in an amount of 0.5 ml/well. Each well was added with 50 μl of a solution of N-acetylbenanomicin B [dissolved at a concentration of 10 mg/ml in dimethyl sulfoxide (DMSO) and then diluted with phosphate buffered saline to varying concentrations of N-acetylbenanomicin B]. Two hours later, MT-4 cells were infected with 50 μl of HIV (1,000–10,000 plaque-forming units) in each well. The plates were incubated for 4 days at 37° C. under 5% $CO_2$. The MT-4 cells were smeared onto slide glasses, dried and fixed with acetone. The presence of HIV antigen-positive cells were detected by the indirect immunofluoroescent assay [Y. Hinuma et al., "Proc. Natl. Acad. Sci. USA," 78, 6476–6480, (1981)]. Thus, cell smears were treated at 37° C. for 30 minutes with serum of AIDS patient as the first antibody. After washing with phosphate buffered saline, the cells were treated at 37° C. for 30 minutes with fluorescent isothiocyanate-conjugated rabbit anti-human immunoglobulin serum (Cappel Laboratories, Cochranville, Pa., USA) as the second antibody. After the cell smears were washed with phosphate buffered saline and covered with a cover glass, the cells were examined under a fluorescence microscope. Percentages of the number of viral antigen-positive cells (namely, immunofluorescent cells where the HIV-associated antigens were expressed) in the total cells were calculated.

Furthermore, cytotoxicity of N-acetylbenanomicin B to the MT-4 cells was estimated by incubating the MT-4 cells at varying concentrations of N-acetylbenanomicin B added and in the absence of HIV but in the same manner of incubation and under the same conditions of incubation of MT-4 cells as those employed in the above-mentioned test procedure of assaying the activity of N-acetylbenanomicin B to inhibit infection of T-cells with HIV.

The results of the above tests of assaying the inhibitory activity of N-acetylbenanomicin B to the HIV-infection as well as the tests of estimating the cytotoxicity of N-acetylbenanomicin B are shown in Table 2 below. For comparison purpose, the parent benanomicin B was tested in the same manner as above.

TABLE 2

| Concentration of test compound ($\mu$g/ml) | N-acetylbenanomicin B | | Benanomicin B (Comparative) | |
|---|---|---|---|---|
| | Viral antigen-positive cells (%) | cytotoxicity | Viral antigen-positive cells (%) | Cytotoxicity |
| 100 | <1 | + (by DMSO) | <1 | + (by DMSO) |
| 30 | <1 | — | <1 | — |
| 10 | 2 | — | 1 | — |
| 3 | 30 | — | 70 | — |
| 1 | 70 | — | 85 | — |
| 0 | >70 | — | >90 | — |

As is apparent from the test results of the above Table 2, it has been confirmed that N-acetylbenanomicin B is free of the cytotoxicity at its concentration of 30 $\mu$g/ml and can significantly reduce the number of viral antigen-positive cells. At concentrations of 1 and 3 $\mu$g/ml, N-acetylbenanomicin B shows an inhibitory activity superior to benanomicin B. Accordingly, it has been confirmed that N-acetylbenanomicin B has a higher activity to inhibit infection of human T-cells with HIV and hence shows an improved activity to inhibit infection of human T-cell with HIV as compared to the parent benanomicin B. Thus, N-acetylbenanomicin B has, in a sense, an antiviral activity against HIV. 4. Acute toxicity of N-acetylbenanomicin B is next described.

When acute toxicity of N-acetylbenanomicin B according to this invention was tested in a mammalian animal upon intravenous administration, it was revealed that the new antibiotic of this invention is of a very low acute toxicity. Thus, in an acute toxicity test where N-acetylbenanomicin B was administered via intravenous route to ICR mice(female, 4-week old, body weight of 19 to 21 g, 3 mice per group), the mice tolerated a dosage of 300 mg/kg of N-acetylbenanomicin B (namely, none of the mice was killed by intravenous administration of N-acetylbenanomicin B at a dose of 300 mg/kg), whereas the mice did not tolerate a dosage of 200 mg/kg of benanomicin B (namely, benanomicin B shows an LD$_{50}$ of about 150 mg/kg upon intravenous administration).

In a second aspect of this invention, there is provided an antifungal composition for therapeutic treatment of a fungal infection in an animal, including human, which comprises an antifungally effective amount of a N-acetylbenanomicin B of formula (I) as defined hereinbefore, or a salt or an ester thereof as active ingredient, in association with a pharmaceutically acceptable solid or liquid carrier.

In a third aspect of this invention, there is provided an antiviral composition for therapeutic treatment of viral infection, which comprises an antivirally effective amount of N-acetylbenanomicin B or a salt or an ester thereof as active ingredient, in association with a solid or liquid carrier for the active ingredient.

According to a further aspect of this invention, there is provided a method for inhibiting viral infection, particularly acquired human immunodeficiency syndrome virus, which comprises treating the virus with N-acetylbenanomicin B or a salt or an ester of N-acetylbenanomicin B in an amount sufficient to inactivate the virus.

The pharmaceutical antifungal or antiviral composition containing the N-acetylbenanomicin B or a salt or an ester thereof as the active ingredient may be formulated into a known manner into a conventional formulation for administration, for example, powder, granules, tablets, pills and capsules for oral administration, as well as intravenously, intramuscularly or subcutaneously injectable solution, and suppositories, using a pharmaceutically acceptable solid or liquid carrier which is suitable for the formulation.

In general, N-acetylbenanomicin B can be administered either orally or parenterally upon its actual administration in the form of an antifungal or antiviral composition.

When the active ingredient compound used according to this invention, namely N-acetylbenanomicin B or a salt or an ester thereof is given either as the antifungal agent or as the antiviral agent against HIV, it can be administered alone or it can be administered in the form of an injection, oral preparation, suppository or the like containing an excipient or carrier as mixed together. Any pharmaceutically acceptable excipient and carrier are available for that purpose. The nature and quantity of the carrier used may vary depending on the administration route and manner. For example, water, ethanol, an animal or vegetable oil such as soybean oil, sesame oil or mineral oil, or a synthetic oil may be used as a liquid carrier. Suitable solid carriers include, for example, a sugar such as maltose or sucrose, an amino acid, a cellulose derivative such as hydroxypropylcellulose, a polysaccharide such as cyclodextrin, a salt of an organic acid such as magnesium stearate, or the like. In the case of the injections, it is generally preferable that the liquid medium of the injections comprises physiological saline, a buffered solution, an aqueous solution of a sugar such as glucose, inositol or mannitol, or a glycol such as ethylene glycol or polyethylene glycol. It is also feasible to formulate a lyophilized preparation containing N-acetylbenanomicin B as the active ingredient mixed along with an excepient, e.g., a sugar such as inositol, mannitol, glucose, mannose, maltose or sucrose or an amino acid such as phenylalanine. Upon administration, such lyophilized preparation may be dissolved in a suitable solvent for injection, for example, sterilized water or an intravenously-administerable liquid such as physiological saline, aqueous solution of glucose, an aqueous solution of electrolytes or an aqueous solution of amino acid.

Although the proportion of N-acetylbenanomicin B present in the formulated composition may widely vary from one preparation to another preparation, it may generally be in a range of 0.1–100% by weight. In the case of an injection, for example, it is generally desirable that the injectionable solution contains the compounds as active ingredient at a concentration of 0.1–20% by weight. For oral administration, the compound as active ingredient may be formulated into tablets, capsules, a powder, granules in combination with the solid carrier or may be formulated into a solution, a dry syrup or the like in combination with the liquid carrier. In capsules, tablets, granules or a powder, the proportion of N-acetylbenanomicin B as the active ingredient present therein may generally be in a range of about 3–100%, preferably 10–100% by weight, with the balance being a carrier.

The dosage of N-acetylbenanomicin B may suitably be determined in account of the age, body weight, symptome of patients and the therapeutic purpose as intended. The therapeutic, i.e., effective dosage of N-acetyl-benanomicin B may be generally in a range of 1–20 mg/kg/day for the parenteral administration and in a range of 5–500 mg/kg/day for the oral administration. This dosage can be administered either continuously or intermittently as as long as the total dosage does not exceed such a specific level that was decided in view of results of animal tests and various circumstances. Similarly, the total dosage given in the parenteral administration may, of course, vary suitable depending on the way of administration, conditions of the patient or animal under treatment, for example, the age, body weight, sex, sensitivity, foods or feed, administration time, administration route, drugs administered concurrently, conditions of the patient and disease. The suitable dosage and administration frequency of N-acetylbenanomicin B under given conditions must be determined by an expert physician through the tests of determining optimal dosage and in light of the above guidelines. These requirements for administration should also applies to the oral administration of N-acetylbenanomicin B.

In another aspect of this invention, there is provided a process for the production of the antifungal and antiviral antibiotic, N-acetylbenanomicin B, which comprises converting chemically an antibiotic, benanomicin B, into N-acetylbenanomicin B.

Here, by the term "converting chemically benanomicin B" is meant acetylation of benanomicin B by acylating the 4"-amino group of benanomicin B with acetic acid or its reactive derivative such as acetic anhydride. The method for preparing the starting benanomicin B is described in the specification of the aforesaid European patent application publication No. 0 315 147 A2, but the preparation of benanomicin B is briefly illustrated hereinafter with reference to Referential Examples 1 to 3.

The acylation, especially acetylation of the 4"-amino group of benanomicin B with acetic acid or its reactive derivative may be carried out according to any of the known methods for synthesis of amides with utilizing the dicyclohexylcarbodiimide method, mixed acid anhydride method, acid chloride method, azide method, active ester method, and the like. However, it is preferred that the acetylation of benanomicin B is effected by reacting benanomicin B with an equimolar proportion or excess of acetic anhydride in a lower alkanol such as methanol and ethanol, or water or a mixture of a lower alkanol with water at ambient temperature. The resulting acetylation product of benanomicin B may be readily isolated and purified by a column chromatography on a conventional non-ionic microporous resin such as "Diaion" HP 10 or HP 20 (products of Mitsubishi Kasei Co. Ltd., Japan) or "Amberlite" XAD-1 or XAD-2 (products of Rhom & Haas Co. Ltd., U.S.A.) or a molecule-sieve resin such as "Sephadex" LH-20 (a product of pharmacia Co., Sweden).

N-acetylbenanomicin B as formed in the reaction solution as described above can be isolated in its free form, namely, as N-acetylbenanomicin B itself. A solution containing N-acetylbenanomicin B or its concentrated solution may be treated with an inorganic base, for example, an alkali metal compound such as sodium hydroxide or potassium hydroxide; an alkaline earth metal compound such as calcium hydroxide or magnesium hydroxide; and an ammonium salt, or an organic base such as ethanolamine, triethylamine or dicyclohexylamine during operation of one step for the recovery and purification. Then, N-acetylbenanomicin B can be converted into the corresponding salt and may further be isolated in the form of the salt. Further, the salt of N-acetylbenanomicin B so produced can then be converted into the free form, namely, N-acetylbenanomicin B itself when treated by a method known per se in the art. In addition, N-acetylbenanomicin B as obtained in the free form may again be converted into a salt by reaction with the above-mentioned base in a usual manner. Further, when reacting N-acetylbenanomicin B with an alcohol, for example, a lower alkanol such as methanol and ethanol, the corresponding ester at its carboxyl group may be formed.

More particularly, salts of N-acetylbenanomicin B of the formula (I) include a pharmaceutically acceptable salt (the carboxylate) of N-acetylbenanomicin B with a pharmaceutically acceptable metal, particularly a pharmaceutically acceptable alkali metal such as sodium and potassium and a pharmaceutically acceptable alkaline earth metal such as calcium and magnesium, and ammonium cation, as well as a pharmaceutically acceptable base-addition salt (at the carboxyl group of the compound) with a pharmaceutically acceptable organic base, particularly an amine, such as a lower ($C_1$–$C_6$) alkyl amine, especially triethylamine, ethanolamine and dicyclohexylamine. Esters of N-acetylbenanomicin B include a pharmaceutically acceptable ester (the carboxylate) with a pharmaceutically acceptable ester-forming radical such as a lower ($C_1$–$C_6$) alkyl group, especially methyl or ethyl; a lower ($C_2$–$C_6$) alkanoyloxy-lower ($C_1$–$C_6$) alkyl group such as acetoxymethyl, 1-acetoxyethyl and pivaloyloxymethyl; or a lower ($C_1$–$C_6$) alkoxycarbonyloxy-lower ($C_1$–$C_6$) alkyl group such as 1-(ethoxycarbonyloxy) ethyl group.

Since benanomicin B which is used as a starting material for the production of N-acetylbenanomicin B is an antibiotic which is produced by cultivation of a new microorganism, MH193-16F4 strain, the fermentative production of this antibiotic is described hereinafter.

The production of benanomicin B may be carried out by inoculating the MH193-16F4 strain of actinomycete to a culture medium containing such nutrient sources which can be utilized by ordinary microorganisms, and then incubating said benanomicin-producing strain under aerobic conditions. Benanomicin B is produced together with benanomicin A and they are accumulated primarily in the culture broth. Benanomicins A and B may be recovered from the resulting culture, especially from the culture broth or its filtrate.

The nutrient sources available in the culture medium to be used may be any of the conventional carbon and nitrogen sources which have been useful as nutrient sources for the cultivation of known strains of actinomycete. For example, the assimilable nitrogen sources may include soybean meal, peptone, meat extract, corn steep liquor, cotton seed meal, peanut meal, dry yeast, yeast extract, NZ-amine, casein, sodium nitrate, ammonium sulfate and ammonium nitrate which are commercially available. The assimilable carbon sources may include glycerin, sucrose, starch, glucose, galactose, maltose, dextrin, lactose, molasses, soybean oil, fats and amino acids, which are commercially available. The culture medium may also contain inorganic salts such as sodium chloride, phosphates, calcium carbonate, magnesium sulfate, cobalt chloride and manganese chloride. In addition, trace amounts of metal salts, and one or more of animal, vegetable or mineral oils can also be added.

Liquid cultivation method is preferred for the production of benanomicins A and B in a large scale. The cultivation temperature may be chosen within the range of the temperatures at which the benanomycins-producing microorganism can grow and can produce benanomicins A and B. The cultivation temperature may generally be at 20°–40° C., preferably at 25°–37° C.

For recovery of benanomicins A and B from the resulting culture of the microorganism capable of producing benanomicins A and B, benanomycins A and B can be extracted from the culture or the culture broth filtrate and then purified by using conventional methods for recovery and purification, for example, solvent extraction, ion-exchange resin method, adsorptive or partition column chromatography, gel filtration, dialysis, precipitation and the like, either singly or in combination. For example, benanomicins A and B can be recovered from the incubated mycelial cake by extacting with acetone-water or methanol-water. On the other hand, benanomicins A and B which have been produced and accumulated in the culture broth or the filtrate can be adsorbed on an adsorbent such as a microporous nonionic resinous adsorbent, for example, "Diaion" HP-20 (trade name; synthetic resinous adsorbent produced by Mitsubishi Kasei Corporation, Japan). In addition, when the culture broth or the broth filtrate is extracted with an organic solvent immiscible with water, e.g., butanol, ethyl acetate or the like, benanomicin A and B substances are extracted in the organic solvent phase.

For the production of benanomicins A and B, it is preferred that the MH193-16F4 strain is cultivated in a culture medium under aerobic conditions at a temperature of 25° to 37° C., preferably for 3 to 10 days, to produce and accumulate benanomicin A and benanomicin B in the resulting culture broth, the culture broth is filtered, and the resultant culture broth filtrate is passed through a column of an adsorbent to effect the adsorption of benanomicin A and benanomicin B by the adsorbent, and benanomicin A and benanomicin B are separately recovered by chromatographically eluting the column of the adsorbent containing benanomicins A and B adsorbed therein.

For mutual isolation and further purification of benanomicins A and B, chromatographic method with use of an adsorbent such as silica gel ("WAKOGEL C-300", trade name, product of Wako Pure Chemical Industries, Ltd.), and alumina or a gel-filtration agent "Sephadex LH-20" (trade name; product of Pharmacia AB), or the like may be made suitably.

Benanomicins A and B as produced in the culture as described above can be isolated as benanomicins A and B as such in their free form.

Incidentally, the MH193-16F4 strain has been deposited in an authorized Japanese depository "Fermentation Research Institute", Agency of Industrial Science and Technology, Ministry of International Trade and Industry, Japanese Government, under the deposit number FERM P-9529 since August 21, 1987. The MH193-16F4 strain has now been deposited in the "Fermentation Research Institute" in terms of the Budapest Treaty under the deposit number "FERM BP-2051". This Japanese depository locates in Tsukuba-city, Ibaragi-ken, Japan.

The following Referential Examples 1 to 3 illustrate the fermentative production of benanomicins A and B.

Referential Example 1

A loopful quantity of the MH193-16F4 strain (identified as FERM BP-2051), which had been incubated in a slant agar medium, was inoculated into 80 ml of a liquid culture medium comprising 1.0% starch and 3.0% soybean meal (pH 7.0 before the sterilization) which was placed in a Sakaguchi's flask of 500 ml-capacity. The inoculated culture medium was incubated at 28° C. for 3 days under rotatory shaking (135 rpm.) to provide a first seed culture. The first seed culture obtained was inoculated in 3 ml-portions into 80 ml-portions of the liquid culture medium having the same composition as above, which were separately placed in many Sakaguchi's flasks. The inoculated culture media were incubated for 3 days under the same incubation conditions as above, to give the second seed culture. The resultant second seed culture (2 liters) was then inoculated to a culture medium (50 liters) of the same composition as above which had been sterilized at 120° C. for 15 minutes and was placed in a tank-fermentor of 100 l-capacity. The so inoculated culture medium was then cultured at 28° C. for 2 days under aeration at a rate of 50 l of air per minute and under agitation at 200 rpm. to effect the submerged cultivation of the MH193-16F4 strain under aerobic conditions and obtain a third seed culture. The resultant third seed culture (12 liters) was inoculated into a productive culture medium (300 liters) comprising 2.0% of glycerin, 1.5% of soybean meal (available commercially under a tradename "Esusan Meat", a product of Ajinomoto Co. Ltd., Japan), 0.0025% of $K_2HPO_4$, 0.1125% of $KH_2PO_4$, 0.005% of $CoCl_2.6H_2O$, 0.03% of a silicone oil "KM72" (an antifoaming agent, a trade name of a product of Shinetsu Chemicals Co. Ltd., Japan) and 0.01% of a surfactant "Adekanol" (a trade name, product of Asahi Denka Kogyo Co. Ltd., Japan) which had preliminarily been sterilized at 125° C. for 30 minutes and was placed in a tank-fermentor of 570 l-capacity. The cultivation was conducted at 28° C. for 7 days under agitation at 300 rpm. and under aeration at a rate of 150 l of air per minute for the first 24 hours of the cultivation and then at a rate of 300 l of air per minute after 24 hours of cultivation. After the completed cultivation, the culture broth obtained was mixed with diatomaceous earth as a filtration-aid and then filtered to give 250 l of the culture broth filtrate (pH 6.0).

Referential Example 2

The culture broth filtrate (250 l) obtained in the above Referential Example 1 was passed through a column of 15 l of a microporous non-ionic adsorbent resin "Diaion" HP-20 to effect the adsorption of the active substances by the adsorbent. After the adsorbent column was washed with 100 l of water and with 45 l of 50% aqueous methanol, the adsorbent column was eluted with 45 l of 70% aqueous methanol and then with 90 l of dry methanol, so that the first fraction (53 l), second fraction (38 l) and third fraction (27 l) of the eluate were obtained separately. The first fraction containing the active substance was concentrated to 3 l under reduced pressure, followed by adjustment to pH 3.5 with dilute hydrochloric acid to deposit a precipitate of a red color. The precipitate was collected by filtration and then dried under reduced pressure, whereby 152 g of a crude brown powder mainly comprising benanomicin A was obtained.

The crude powder (150 g) was dissolved in 600 ml of dimethylformamide. After saturation of the resultant solution with water vapor at room temperature for 3 days in a desiccator, a crystalline precipitate was deposited. The precipitate was collected by filtration and then dried under reduced pressure, thereby obtaining 29 g of benanomicin A-dimethylformamide solvate. The second fraction of the eluate was processed in the same way as the first fraction, thereby obtaining 14 g of benanomicin A-dimethylformamide solvate.

One gram of the benanomicin A-dimethylformamide solvate as obtained from said first fraction was dissolved in dimethyl sulfoxide (5 ml). The resultant solution was added dropwise under stirring into 300 ml of methanol, followed by stirring for 10 minutes to deposit a precipitate of a reddish brown color. The precipitate was filtered out and then dried under reduced pressure, to afford 935 mg of a purified benanomicin A as reddish brown powder.

Referential Example 3

The third fraction of the eluate as obtained in the Referential Example 2 was concentrated to 1.5 l under reduced pressure, followed by its adjustment to pH 3.5 with dilute hydrochloric acid, to obtain a precipitate of red color. The precipitate was collected by filtration and then dried under reduced pressure, whereby 98 g of a crude brown powder containing benanomicin B was obtained. One gram of this crude powder was dissolved in 10 ml of dimethylformamide at 40° C. and the resulting solution was passed through a column of 1 l. of a gel-filtration agent "Sephadex" LH-20 which had been soaked with dimethylformamide, and then the "Sephadex" column was developed with dimethylformamide. The eluate was collected in 6 ml-fractions. Fraction Nos. 64–72 containing the active substance were collected, combined and then concentrated to dryness under reduced pressure, whereby 657 mg of a crude brown powder comprising benanomicin B-dimethylformamide solvate was obtained. Three hundred milligrams of this crude powder were dissolved in 100 ml of methanol, and after addition of 1 ml of 1 N hydrochloric acid, the solution was concentrated to dryness under reduced pressure. The resultant crude powder of a brown color was dissolved in 3 ml of dimethyl sulfoxide. The resulting solution was added dropwise to 200 ml of chloroform under stirring, followed by stirring for 20 minutes to deposit a reddish brown precipitate. The precipitate was collected by filtration and then dried under reduced pressure, to yield 258 mg of benanomicin B hydrochloride in a purified form.

This invention is now illustrated with reference to the following Examples, to which this invention is not limited in any way. Thus, the detailed properties of N-acetylbenanomicin B have been made evident by this invention and hence it is feasible for the skilled in the art to contemplate and perform the process of producing N-acetylbenanomicin B in different ways with taking into account the above-described properties of N-acetylbenanomicin B. Accordingly, this invention embraces not only any modification of the procedures of the following Examples, but also all such processes wherein N-acetylbenanomicin B is produced, concentrated, extracted and/or purified in a manner known per se with utilizing the properties of N-acetylbenanomicin B.

Example 1

Benanomicin B hydrochloride (125 mg) was dissolved in 10 ml of an aqueous solution of 0.1 M sodium carbonate, and to the resulting solution was added 0.1 ml of acetic anhydride. The mixture obtained was stirred at ambient temperature for 20 minutes. The resultant reaction solution was then adjusted to pH 4.0 by addition of 1 M hydrochloric acid and subsequently passed through a column of 20 ml of a non-ionic microporous adsorbent resin, "Diaion" HP-20 (a product of Mitsubishi Kasei Co., Japan) to adsorb the acetylation product of benanomicin B by the resin. The resin column was washed with water and developed with aqueous 80% acetone. The red colored fractions of the eluate were combined together and concentrated to dryness. The residue obtained was dissolved in methanol and the methanolic solution was passed through a column of a molecule-sieve agent, "Sephadex" LH-20 (a product of Pharmacia Co., Sweden), followed by development with methanol. The eluate which showed a single spot of red color on a thin layer chromatography on a silica gel plate was concentrated to dryness. N-acetylbenanomicin B (118 mg) was obtained as a reddish brown colored powder which showed a melting point of higher than 200° C.

Example 2

A solution of N-acetylbenanomicin B (89 mg) in a mixture of 10 ml of water and 1.1 ml of 0.1 M NaOH was lyophilized. The lyophile was dissolved in 3 ml of methanol and chromatographed on a column of "Sephadex" LH-20 (300 ml) developed with methanol to obtain N-acetylbenanomicin B sodium salt (80 mg) as a reddish brown powder.

Example 3

A solution of N-acetylbenanomicin B (89 mg) in a mixture of 500 ml of methanol and 1 ml of 1 M HCl was stirred at room temperature for 15 hours, and then the reaction mixture was concentrated to dryness. The residue was dissolved in 1 ml of dimethyl sulfoxide and chromatographed on a column of "Sephadex" LH-20 (500 ml) developed with methanol. The first reddish eluate was concentrated to obtain N-acetylbenanomicin B methyl ester (60 mg) as a reddish brown powder.

This invention is further illustrated with reference to the following Examples which show various forms of the preparations or compositions containing N-acetylbenanomicin B according to this invention.

Example 4

An amount of purified water was added to 10 parts by weight of sodium salt (the carboxylate) of N-acetylbenanomicin B to give a total of 1,000 parts by weight. After dissolution of the sodium salt in water, the solution thus prepared was subjected to sterilizing filtration by passing through a microporous filter of a tradename "Millipore Filter GS". Five grams of the sterile filtrate obtained were taken into each 10 ml vial and then lyophilized, to obtain a lyophilized preparation for injection which contained 50 mg of sodium salt of N-acetylbenanomicin B per vial.

Example 5

Fifty parts by weight of N-acetylbenanomicin B, 600 parts by weight of lactose, 330 parts by weight of crystalline cellulose and 20 parts by weight of hydroxypropylcellulose were mixed together thoroughly. The resultant powdery mixture was pressed by a roll-type pressing machine (Roller Compactor, trade mark) and then the resulting compressed solids were crushed. The thus-crushed material was sifted. The fraction of the granules which were of sizes between 16 mesh and 60 mesh was collected as granular preparation.

Example 6

Thirty parts by weight of N-acetylbenanomicin B, 120 parts by weight of crystalline lactose, 147 parts by weight of crystalline cellulose and 3 parts by weight of magnesium stearate were mixed in a V-model mixer and compressed into tablets each containing 300 mg of N-acetylbenanomicin B as the active ingredient per tablet.

We claim:

1. An antifungal and antiviral antibiotic, N-acetylbenanomicin B having the formula (I)

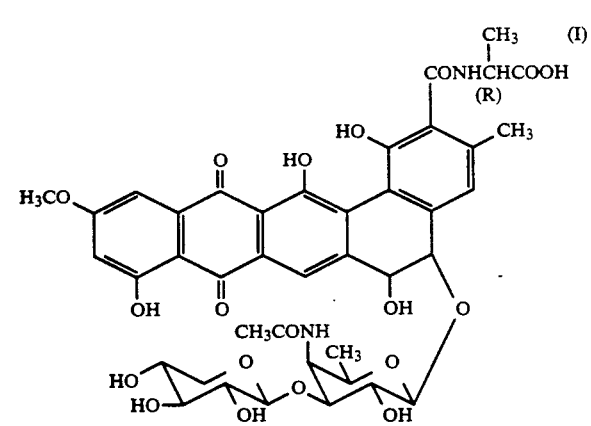

or a salt or an ester thereof.

2. A compound as claimed in claim 1, which is in the form of a salt thereof with an alkali metal or an alkaline earth metal or in the form of an ester thereof with a lower alkyl group, a lower alkanoyloxy-lower alkyl group, or a lower alkoxycarbonyloxy-lower alkyl group.

3. The compound of claim 2, wherein said compound comprises a carboxylate salt.

4. The compound of claim 2, wherein said compound comprises a carboxylate ester.

5. The compound of claim 2, wherein said compound comprises a carboxylate ester with a lower alkanoyloxy-lower alkyl group selected from the group consisting of acetoxymethyl, 1-acetoxyethyl and pivaloyloxymethyl.

6. The compound of claim 2, wherein said compound comprises a carboxylate ester with a 1-(ethoxycarbonyloxy)ethyl group.

7. An antifungal or antiviral composition for therapeutic treatment of a fungal or viral infection in an animal, including human, which comprises an antifungally or antivirally effective amount of N-acetylbenanomicin B having the formula (I):

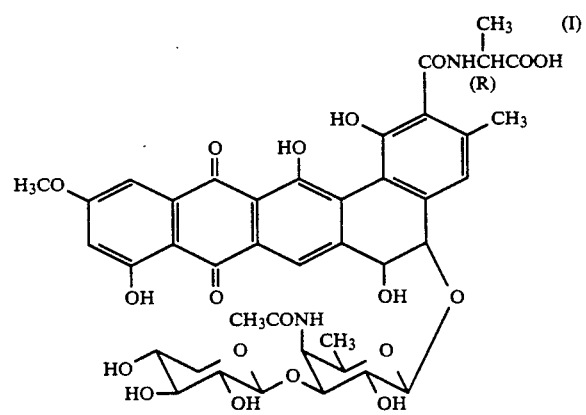

or a salt or an ester thereof in a solid or liquid carrier.

8. A process for producing N-acetylbenanomicin B having the formula (I):

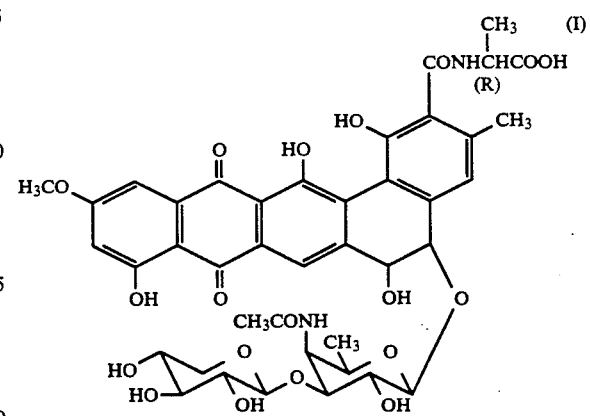

comprising reacting benanomicin B with acetic anhydride in a lower alkanol or water or a mixture of a lower alkanol with water.

9. A method for treating a virus in vitro which comprises treating the virus in vitro with N-acetylbenanomicin B having the formula (I):

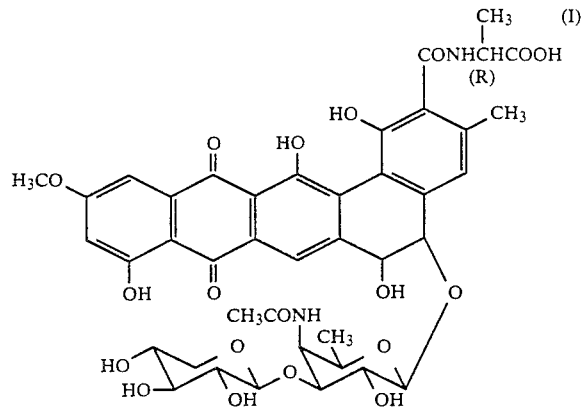
or a salt or ester thereof in an amount sufficient to inhibit the virus.
10. The method of claim 9, wherein the virus is the acquired human immunodeficiency virus.
* * * * *